United States Patent
Maguire

(10) Patent No.: US 10,912,881 B2
(45) Date of Patent: Feb. 9, 2021

(54) IMPLANTABLE INFUSION PUMPING CATHETER

(71) Applicant: Shane Maguire, St. Paul, MN (US)

(72) Inventor: Shane Maguire, St. Paul, MN (US)

(73) Assignee: Shane Maguire, St. Paul, MN (US)

(\*) Notice: Subject to any disclaimer, the term of this patent is extended or adjusted under 35 U.S.C. 154(b) by 319 days.

(21) Appl. No.: 15/569,853

(22) PCT Filed: Apr. 26, 2016

(86) PCT No.: PCT/US2016/029331
§ 371 (c)(1),
(2) Date: Oct. 27, 2017

(87) PCT Pub. No.: WO2016/176192
PCT Pub. Date: Nov. 3, 2016

(65) Prior Publication Data
US 2018/0117243 A1    May 3, 2018

Related U.S. Application Data

(60) Provisional application No. 62/153,062, filed on Apr. 27, 2015.

(51) Int. Cl.
*A61M 5/142* (2006.01)
*A61M 25/00* (2006.01)

(52) U.S. Cl.
CPC .... *A61M 5/14228* (2013.01); *A61M 5/14276* (2013.01); *A61M 2025/0025* (2013.01);
(Continued)

(58) Field of Classification Search
CPC .............. A61M 5/142; A61M 5/14212; A61M 5/14224; A61M 5/14228; A61M 5/14276;
(Continued)

(56) References Cited

U.S. PATENT DOCUMENTS

| 4,509,947 A | 4/1985 | Lattin |
| 4,944,659 A | 7/1990 | Labbe et al. |

(Continued)

FOREIGN PATENT DOCUMENTS

| CN | 1565662 A | 1/2005 |
| EP | 1513580 B1 | 3/2009 |

(Continued)

OTHER PUBLICATIONS

Bartels Micropumps, online Brochure posted Feb. 24, 2014, Bartels Mikrotechnik GmbH, Emil-Figge-Str. 76a, 44227 Dortmund, Germany (Year: 2014).*

(Continued)

*Primary Examiner* — Bhisma Mehta
*Assistant Examiner* — James D Ponton
(74) *Attorney, Agent, or Firm* — Schwegman Lundberg & Woessner, P.A.

(57) ABSTRACT

In some examples, an implantable infusion device (100) using a piezoelectric and/or electrostrictive mechanical pumping catheter (10) includes a reservoir (109) configured to retain for a fluid to be dispensed within a patient, at least one piezoelectric and/or electrostrictive mechanical pumping catheter for dispensing the fluid contained within the reservoir, a transceiver, and a processor (103) to regulate control the operation of the piezoelectric and/or electrostrictive mechanical pumping catheter.

23 Claims, 9 Drawing Sheets

(52) U.S. Cl.
    CPC .............. *A61M 2205/825* (2013.01); *A61M 2205/8212* (2013.01); *A61M 2205/8243* (2013.01)

(58) Field of Classification Search
    CPC ........... A61M 2025/0025; A61M 2025/14208; A61M 2205/8212
    See application file for complete search history.

(56) References Cited

U.S. PATENT DOCUMENTS

| | | |
|---|---|---|
| 6,228,046 B1 | 5/2001 | Brisken |
| 6,283,949 B1 | 9/2001 | Roorda |
| 6,723,072 B2 | 4/2004 | Flaherty et al. |
| 7,601,148 B2 | 10/2009 | Keller |
| 7,608,060 B2 | 10/2009 | Gillespie, Jr. et al. |
| 7,896,866 B1 | 3/2011 | Blischak |
| 8,353,872 B2 | 1/2013 | Kawamura |
| 8,382,703 B1 | 2/2013 | Abdelaal |
| 2002/0087114 A1* | 7/2002 | Hartlaub ............ A61M 5/14276 604/65 |
| 2004/0082908 A1 | 4/2004 | Whitehurst et al. |
| 2005/0177111 A1 | 8/2005 | Ozeri et al. |
| 2006/0259016 A1* | 11/2006 | Steinbach ............ A61K 9/0024 604/891.1 |
| 2008/0132842 A1 | 6/2008 | Flaherty |
| 2008/0208173 A1 | 8/2008 | Lee et al. |
| 2008/0255517 A1 | 10/2008 | Nair et al. |
| 2009/0112155 A1 | 4/2009 | Zhao et al. |
| 2009/0137957 A1 | 5/2009 | Wagener |
| 2013/0303971 A1* | 11/2013 | Budgett .............. A61M 27/006 604/9 |
| 2014/0199181 A1 | 7/2014 | Chappel |

FOREIGN PATENT DOCUMENTS

| | | |
|---|---|---|
| WO | WO-2005074374 A1 | 8/2005 |
| WO | WO-2011116393 A1 | 9/2011 |
| WO | WO-2012033420 A2 | 3/2012 |
| WO | WO-2016176192 A1 | 11/2016 |

OTHER PUBLICATIONS

"Application Serial No. PCT/US2016/029331, Invitation to Pay Add'l Fees and Partial Search Report dated Aug. 9, 2016", 5 pgs.
"International Application Serial No. PCT/US2016/029331, International Search Report dated Oct. 10, 2016", 8 pgs.
"International Application Serial No. PCT/US2016/029331, Written Opinion dated Oct. 10, 2016", 8 pgs.
Gonzalez, Ulises F., et al., "Simulation of Mems Piezoelectric Micropump for Biomedical Applications", (2002), 11 pgs.

* cited by examiner

IMPLANTABLE INFUSION PUMPING CATHETER

PRIORITY

This application is a U.S. National Stage Filing under 35 U.S.C. 371 from International Application No. PCT/US2016/029331, filed on Apr. 26, 2016, and published as WO2016/176192 on Nov. 3, 2016, which claims the benefit of U.S. Provisional Patent Application No. 62/153,062, titled "PIEZOELECTRIC AND/OR ELECTROSTRICTIVE MECHANICAL IMPLANTABLE INFUSION PUMPING CATHETER," by Shane Maguire, and filed on Apr. 27, 2015, all of which are incorporated herein by reference in their entirety.

TECHNICAL FIELD

This disclosure pertains generally, but not by way of limitation, to medication delivery devices and more specifically to implantable infusion devices.

BACKGROUND

It can be important to provide a localized implantable delivery system in order to accurately present a medication, drug, or other fluid to a specific region, or target site, of a patient. By delivering the drug or other fluid to the target site, a much lower dose can be given to the patient, which can potentially avoid adverse side effects that can be caused by oral or injected administration of a medication or other fluid.

Localized and controlled infusion of drugs or other fluids at their desired site of action can be preferable over other delivery approaches because it can reduce toxicity and increase treatment efficiency. Localized infusion has increasingly become important for a multitude of medical applications including, but not limited to: 1) cancer and neurodegenerative disorder treatment, 2) pain management, 3) tissue engineering, 4) localized vascular and nervous system therapy.

Implantable infusion devices e.g., drug infusion pumps, were created to minimize the negative aspects such as infection and needle migration of therapies that require external pump and catheter systems. Implantable infusion devices developed to date typically include 1) a drug reservoir to contain the drug, 2) a control/circuit board, 3) wireless communication/telemetry circuitry, 4) an injection port to inject drug into the reservoir, 5) an additional troubleshooting port for access to the catheter, and 6) the ability to connect and/or use a catheter to deliver the drug to the intended site. Additionally, internal pumps can provide the ability to bypass the blood brain barrier and thus can allow for a hundredth, a thousandth, or even less, of the normal oral dose.

Localized delivery of the drug to a target site can be achieved by manual delivery, but this can include repeated injections at the target site or delivery of the drug via a time released drug formulation. The negative aspects of a time released drug can include drug stability issues depending upon the duration of time over which the drug must be delivered and the ability to have an accurately controlled delivery of the desired volume. Additionally, the volume of drug used for intravascular delivery can often require an order of magnitude or more of the drug to be infused into the patient than that required for intrathecal delivery. This can avoid many of the drug side effects that are normally generated by the larger doses of oral or even intravenously delivered drugs.

Existing external infusion systems include those mounted on an external support or worn by the patient, using a drug pump and catheter combination. Potential issues with patient use and adoption with these systems can include the following: 1) potential infection at the site of entry into the patient's body, 2) recurrent battery replacement or tethered power supply, and 3) aesthetic and acceptance concerns by the patients regarding appearance. Additionally, with these systems, the patient may live a restricted lifestyle because of being tethered to an external device.

Recent approaches can infuse medicine to the target site via an implanted drug infusion pump and attached catheter system that allows the drug to be delivered directly to the desired site. Typically, these approaches use pneumatic, mechanical, electromagnetic, piston driven, and watch motor style pumps (gear driven) for delivering the selected drug to the site of interest. Implantable piston or gear driven based pumps can be bulky and prone to mechanical wear and corrosion which may lead to premature failure and the need to surgically remove/replace the drug delivery device.

Drug delivery devices can be programmed to infuse a variety of dosages that can be delivered at a rate from constant to widely variable over time. The rate (dosage over time) can be programmed using electronics (processor, memory, etc.) contained within the electronic section of the pump. Typically, programming is performed via an external programming device. The speed/rate of delivery is controlled by the rate the piezo/electrostrictive elements are commanded to open/close as well by the dimensions and flexation capabilities of the piezo/electrostrictive material in the pumping catheter segments.

Overview

In an example, this disclosure relates to an implantable infusion device using a piezoelectric and/or electrostrictive mechanical pumping catheter. The implantable piezoelectric and/or electrostrictive infusion catheter is comprised primarily of from two to any number of piezoelectric and/or electrostrictive pumping segments running independently, controllable in any order/sequence, and a reservoir from which a fluid, gas, etc. is to be dispensed. The piezoelectric and/or electrostrictive mechanical catheter for dispensing the fluid/gas contained within the reservoir acts as a fluid/gas transfer conduit working together with a transceiver, an optional energy harvesting circuitry, a wireless communication (telemetry) receive/send circuit, and an integrated circuit to regulate the operation of the piezoelectric and/or electrostrictive mechanical pumping catheter.

In some examples, this disclosure is directed to a pumping catheter that comprises a tubular member defining a lumen, the tubular member having a proximal end, a distal end, and a plurality of deformable segments extending therebetween; and at least one pump positioned in at least one of the plurality of deformable segments, wherein the at least one pump is configured to receive a control signal and, in response, controllably deform at least one segment to control at least one of a rate of fluid flow through the lumen and a volume of fluid through the lumen.

In some examples, this disclosure is directed to an implantable infusion device, comprising a reservoir configured to retain a fluid to be dispensed within a patient; at least one piezoelectric and/or electrostrictive mechanical pumping catheter for dispensing the fluid contained within the reservoir; a transceiver; and a processor to control operation of the piezoelectric and/or electrostrictive mechanical pumping catheter.

This overview is intended to provide a summary of the subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1A:
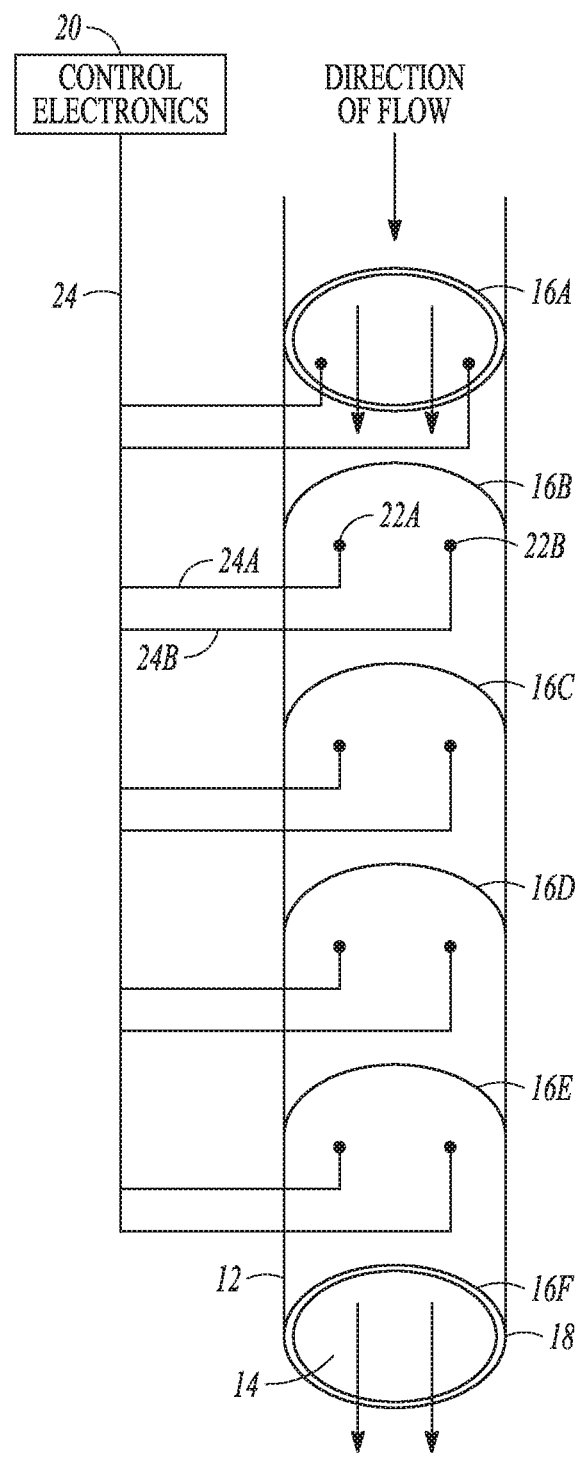
FIG. 1A is a conceptual view of an example of a portion of a piezoelectric and/or electrostrictive mechanical pumping catheter for controlling fluid flow, in accordance with this disclosure.

As noted above, existing implantable infusion devices can suffer a drawback in their large and rigid design confining them to only be implanted in specific locations. Also, pneumatic, gear driven, or electromagnetic motorized piston driven pumps can consume large amounts of power, leading to a continual need to recharge if the pump is powered by a rechargeable source (i.e., Li-Ion battery) or replace the device when power is diminished to a level requiring replacement sooner than desired if the pump is powered by a primary source (i.e., Lithium battery). The frequency of recharge or replacement can be dependent upon the use of the implantable infusion device. Recharge may, for example, occur every eight to twenty-four hours and replacement (e.g., surgery to remove and implant another infusion pump) may occur every two to three years. Incorporation of a piezoelectric and/or electrostrictive mechanical pump may increase, e.g., double, or potentially triple, the operational time of the implantable infusion device before a recharge or replacement is required.

This disclosure describes implantable infusion devices that can utilize various piezoelectric and/or electrostrictive pumping techniques. Piezoelectric (also referred to as "piezo" in this disclosure) and/or electrostrictive infusion devices as described in this disclosure can provide several advantages over existing pumps including those using rotational motor driven pumping, mechanisms, including, but not limited to: 1) reduction in size, 2) enablement of a flexible design, 3) implantable in a multitude of locations within different sized patients including infants and small children, 4) low energy consumption (requiring less time to power and recharge and/or less frequent replacement), 5) low maintenance, 6) the introduction of energy harvesting enhancements and operation, and 7) the combination of piezo-electrical and/or electrostrictive pumping material into the design of a "catheter" based delivery system that incorporates the usage of single to multiple piezo and/or electrostrictive components that function in a singular or plurality acting in parallel, series, or various specific orders of compression and release to pump fluid from a reservoir to a target area.

Minimizing the size of the system, and avoiding the bulk of existing systems, can allow the devices described in this disclosure to support new implant locations previously not feasible with existing infusion system. Examples of new implant locations, in addition to the typical locations of the chest and buttock can include, but are not limited to, appendages (e.g., legs and arms), shoulders, back, and the head. Additionally, the system described in this disclosure can open an important, new arena of implantable device usage, thereby allowing implantation in infant and smaller patients due to the small size enabled by this design.

Note: Processors 102 and 103 can be combined into a single processor, whereby references to 103 can be considered the same as 102. Additionally, processors 202 and 203 can be combined into a single processor, whereby references to 203 can be considered the same as 202.

FIG. 1A is a conceptual view of an example of a portion of a piezoelectric and/or electrostrictive mechanical pumping catheter 10 for controlling fluid flow, in accordance with this disclosure. As described in detail in this disclosure, the pumping catheter 10 can include a tubular member 12 defining a lumen 14 with proximal and distal ends and disposed about a plurality of deformable segments 16A-16F (referred to collectively as segments 16), where each segment 16 can include a piezoelectric and/or electrostrictive pump, and a sheath 18, e.g., a biocompatible sheath, disposed about at least the plurality of segments. In addition, the pumping catheter 10 can include a single check valve, or plurality of check valves (not depicted), housed in the proximal and distal ends, and in some configurations, distributed along the length of the pumping catheter between each of the pumping segments, to control fluid flow. Although six segments 16 are depicted in FIG. 1A, the catheter 10 can include more than six segments 16, or fewer than six segments 16.

Figure 1B:
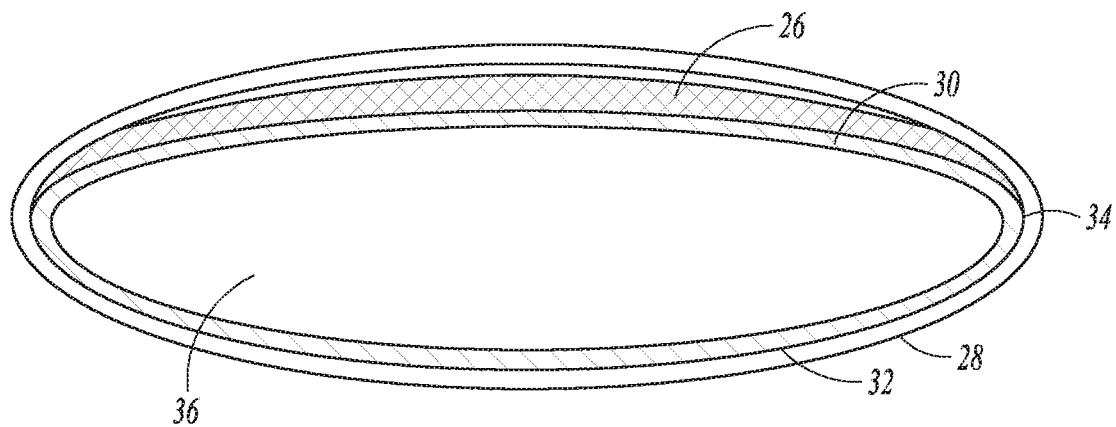
FIGS. 1B and 1C depict cross-sectional end views illustrating examples of piezoelectric and/or electrostrictive pumping segments deforming an interior of the catheter to pump a fluid, e.g., a therapeutic drug, through the lumen of the catheter.
Figure 1C:
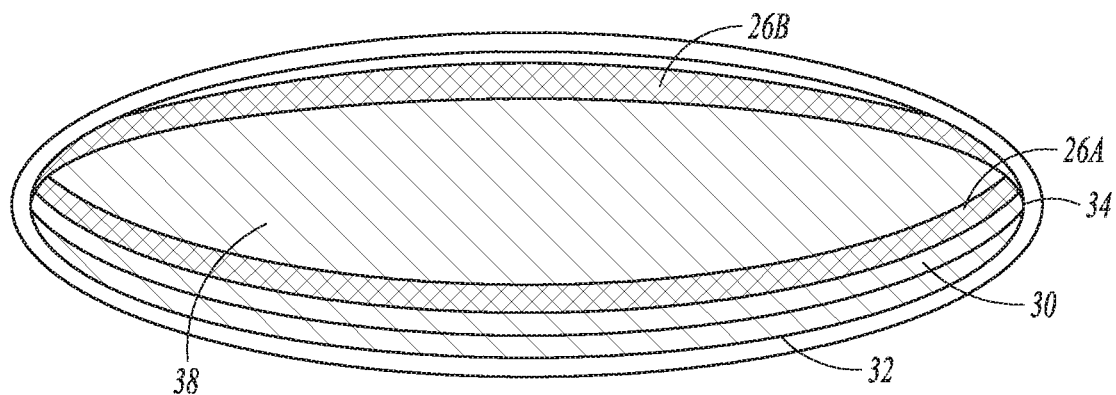

The piezoelectric and/or electrostrictive pumping catheter 10 can include one or more piezoelectric and/or electrostrictive pumping segments 16. In example configurations that include a plurality of piezoelectric and/or electrostrictive segments 16, such as shown in FIGS. 1A-1C, the segments 16 can be arranged in series along the length of the catheter 10 and can be controlled independently.

In some example configurations, the segments 16 can be configured to operate independently of each other, thereby forcing the fluid through the catheter. In some examples, the segments 16 can be substantially adjacent, e.g., one micron or less, to one another in the series. In other examples, the segments 16 can be spaced apart from one another in the series. In some example configurations, a check valve can be placed between each of the pumping segments to further control any backflow between these segments.

Each piezo segment 16 can include, for example, a piezoelectric material engaged to at least two electrical contacts. Non-limiting examples of piezoelectric materials include quartz ($SiO_2$), as well as lithium tantalite, polyvinylidene fluoride, and potassium sodium tartrate. Lead-free piezoelectric materials that can be used in various example implementations include ceramics with a perovskite structure as ceramics with a tungsten bronze structure. Other example piezoelectric materials can include: $BaTiO3$, $KNbO3$, $Ba2NaNb5O5$, $LiNbO3$, $Pb(ZrTi)O3$, $Pb2KNb5O15$, $BiFeO3$, and $NaxWO3$. When control electronics 20 applies a voltage between at least two electrodes/contacts 22A, 22B using wires 24A, 24B (collectively referred to as wires 24) in communication with the control circuitry 20, the piezoelectric material of the deformable segment can flex, e.g., inwardly or outwardly, to close or open the segment 16, respectively. In this manner, the piezoelectric materials are configured to receive control signals and, in response, controllably deform their respective segments to control a rate of fluid flow through the catheter lumen and/or a volume of fluid through the lumen.

Instead of or in addition to piezoelectric materials, electrostrictive materials can be used to implement various techniques of this disclosure. Electrostrictive materials have properties that are similar to piezoelectric materials and can produce a mechanical change, e.g., deformation, in response to the application of an electric field.

Instead of or in addition to piezoelectric and electrostrictive materials, electroactive polymers ("EAP") can be used to implement various techniques of this disclosure. Electroactive polymers can be deformed when an electric field is applied.

In some examples, the segments 16 can have a "normal" (or natural) state such as a normally open state or normally closed state. A normally open state is one in which, absent the application of a voltage to the piezo material and/or electrostrictive on the segment, the segment is open and allows fluid to flow through it. A normally closed state is one in which, absent the application of a voltage to the piezo and/or electrostrictive material on the segment, the segment is closed and prevents fluid from flowing through the segment.

Using the techniques of this disclosure, one or more of the piezo and/or electrostrictive segments 16 can be used to create a piezoelectric and/or electrostrictive pumping catheter 10. In the example shown in FIG. 1A, for example, a plurality of segments 16 can be longitudinally positioned along the length of the catheter 10 and controlled by the control electronics 20 to create a pumping action that can pump fluid from a proximal reservoir (not depicted in FIG. 1A) to a distal connection point or catheter delivery point.

As a voltage signal (or control signal) is applied across the contacts 22A, 22B engaged to the piezo and/or electrostrictive material of a normally closed ("NC") segment, the segment 16 can open and as a voltage signal is applied across the contacts engaged to the piezo and/or electrostrictive material of a normally open ("NO") segment, the segment 16 can close. A control signal may be application of a voltage, current, magnetic field, electric field, or any combination thereof. The control electronics 20 can control the timing and coordination of the voltage signals applied to the piezo and/or electrostrictive segments to create a pumping action.

For example, in the non-limiting example configuration shown in FIG. 1A, the direction of the fluid flow is from the top of the figure (from a fluid reservoir) through six piezo and/or electrostrictive segments (segments 16A-16F). Some example configurations can include more or less than six piezo and/or electrostrictive segments.

The control electronics 20 can apply a first voltage signal to NC segment 16A, which can cause segment 16A to open and draw in fluid. The control electronics 20 can remove the voltage signal to NC segment 16A, which can cause segment 16A to return to its normally closed state and push the portion of the fluid into NO segment 16B. The control electronics 20 can apply a second voltage signal to NO segment 16B, which can cause segment 16B to close and push the portion of the fluid into NO segment 16C. The control electronics 20 can apply a third voltage signal to NO segment 16C, which can cause segment 16C to close and push the portion of the fluid into NO segment 16D. The control electronics 20 can apply a fourth voltage signal to NO segment 16D, which can cause segment 16D to close and push the portion of the fluid into NO segment 16E. The control electronics 20 can apply a fifth voltage signal to NO segment 16E, which can cause segment 16E to close, and the control electronics 20 can apply a sixth voltage signal to NC segment 16F, which can cause segment 16F to open, which will push the portion of the fluid into NC segment 16F. The control electronics 20 can remove the voltage signal to NC segment 16F, which can cause segment 16F to return to its normally closed state and push the portion of the fluid out of the distal tip of the catheter, for example.

FIGS. 1B and 1C depict cross-sectional end views illustrating examples of the piezoelectric and/or electrostrictive pumping segments 16 deforming an interior of the catheter 10 to pump a fluid, e.g., a therapeutic drug, through the lumen of the catheter 10. In the example shown in FIG. 1B, the catheter 10 can include an outer tube 28, e.g., a tube made of Kevlar® (manufactured by DuPont) or similar high tensile strength, but fully flexible, material, and an inner seal tube (layer) 30. In some example configurations, the bottom 32 of the inner seal tube 30 flexes minimally or not at all. The catheter 10 can include flex points 34 on one or both sides of the outer tube 28 and the inner tube 30. A fluid 36, e.g., a therapeutic drug, is depicted in the lumen of the catheter 10. At the top of the catheter 10 and disposed between the outer tube 28 and the inner tube 30 is piezoelectric and/or electrostrictive material 26 forming, for example, a plurality of piezoelectric and/or electrostrictive pumps or pumping segments 16 of the pumping catheter 10.

In the example shown in FIG. 1C, a first piezoelectric and/or electrostrictive material 26A is shown compressing the inner seal tube 30 in a first segment, e.g., in a first segment 16F, into a closed position during pumping action to prevent backflow. A second piezoelectric and/or electrostrictive material 26B of an adjacent second segment is also depicted, e.g., a second segment 16E. The catheter 10 can further include a membrane wall 38 positioned between adjacent segment 16. As seen in FIG. 1C, the membrane wall 38 can stretch to seal the catheter 10 at a segment 16 to prevent backflow.

As an alternative to piezoelectric materials, electrostrictive materials, and electroactive polymers ("EAP"), shape-memory alloys (also referred to as memory metal or memory alloy) can be used in the pumping catheter of FIGS. 1A-1C (and in the system of FIG. 4 below). Shape-memory alloys, e.g., nickel-titanium, exhibit "shape memory" such that the alloy can return to an original shape after deformation, e.g., when the alloy is heated.

Referring to FIGS. 1A-1C, instead of using piezoelectric and/or electrostrictive material 26 in segments 16, each segment 16 can include a shape-memory alloy (SMA) 26. In each segment 16, the SMA 26 can be affixed to a portion of the inner seal tube 30. In an example configuration, the SMA 26 of each segment 16 can have an original state like material 26A in FIG. 1C, where the material 26A compresses the inner seal tube 30 into a closed position. As a tubular structure, the resilient inner seal tube 30 can naturally bias the SMA 26 of each segment outwardly, however, to deform the SMA 26 into a second, open position, like the material 26B in FIG. 1C. To reset the SMA 26 such that it returns to its original, closed state, control electronics 20 can apply a voltage to the SMA 26 via the wires 24, which can heat the SMA 26 sufficiently for it to recover its shape and close the segment.

Figure 2:
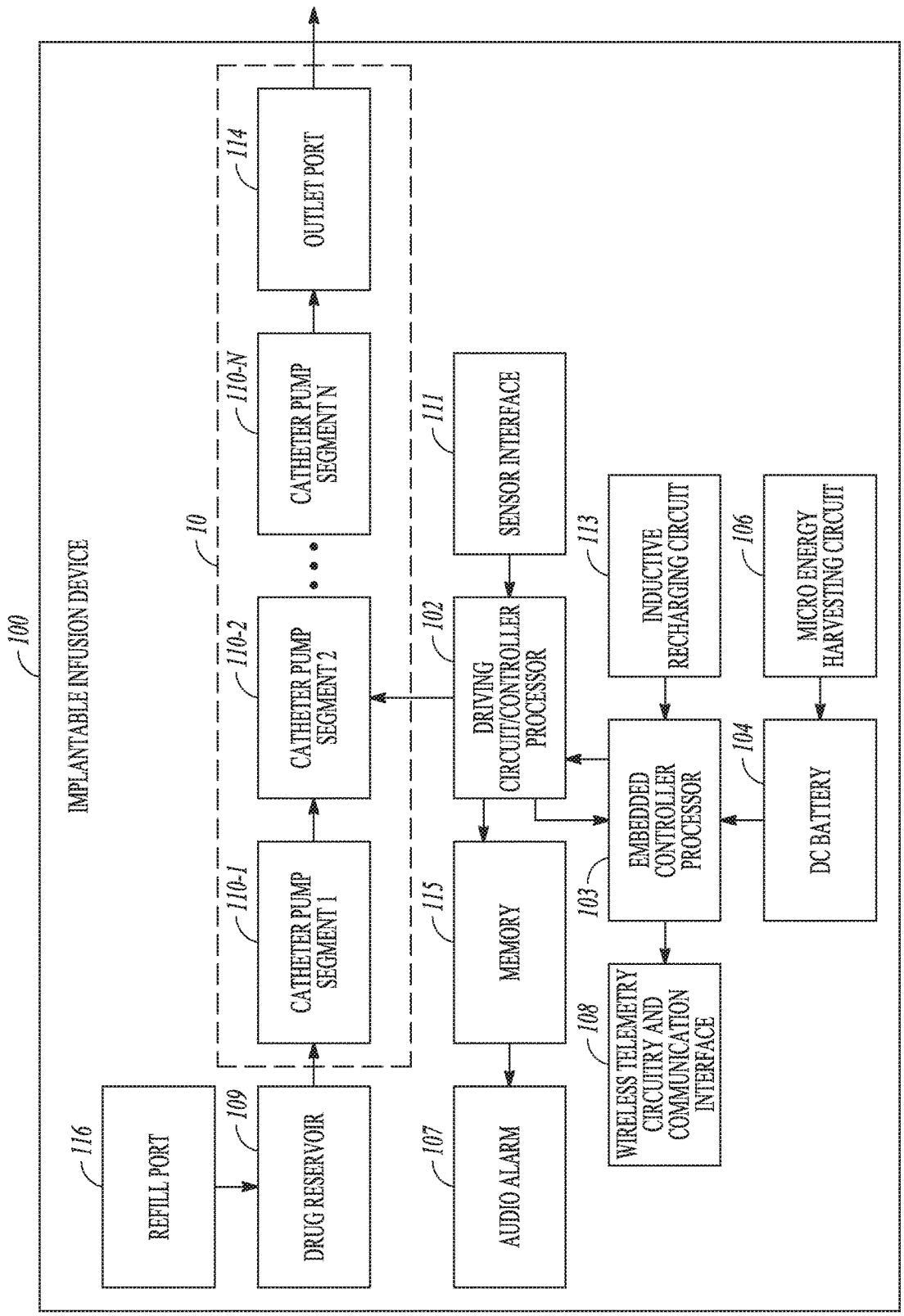
FIG. 2 is a block diagram depicting an example implantable infusion device using a piezoelectric and/or electrostrictive mechanical pumping catheter, e.g., the piezoelectric and/or electrostrictive mechanical pumping catheter of FIG. 1A.

FIG. 2 is a block diagram depicting an example implantable infusion device 100 using a piezoelectric and/or electrostrictive mechanical pumping catheter, e.g., the piezoelectric and/or electrostrictive mechanical pumping catheter of FIG. 1A. The control electronics 20 depicting in various figures of this disclosure can include one or more components depicted in FIG. 2 (or FIG. 7 below). The implantable infusion device or system 100 can include a first processor 103, e.g., an embedded controller/processor, to control power and communication functionality associated with a power source 104, e.g., battery, a recharge circuit 113 for recharging the power source 104, an energy harvesting circuit 106, and a communication interface 108. In some examples, the power source 104 can be a low voltage battery, e.g., about 3 volts.

The device 100 can further include a second processor 202, or incorporate this functionality into processor 103 to control, or be in communication with, a piezoelectric and/or electrostrictive mechanical pumping catheter, such as pumping catheter 10 shown in FIGS. 1A-1C, that can include N number of segments 110-1 through 110-N, a drug reservoir 109, an alarm 107, and a sensing interface 111, configured to receive information from one or more sensors, including biological sensors such as, but not limited to, heart rate, blood pressure, blood oxygenation, motion (roll, pitch, yaw, x, y, x, speed, etc.) sensors including but not limited to GPS, gyro, rate, rotational, and body temperature.

The implantable infusion device 100 can include one or more of the storage devices, communication and alarm/sensing interfaces, power sources, piezoelectric and/or electrostrictive mechanical pumps, reservoirs, and recharge and energy harvesting circuits.

The reservoir 109 can be constructed of one or more materials, including but not limited to silicon, titanium, synthetic fibers such as Kevlar®, and various braided sheathing constructions. The reservoir can be a hard, rigid, or flexible container in various example configurations.

Catheter segments 110-1 through 110-N may be made from a biocompatible material or uniformly coated with a biocompatible material to attain a specified biocompatibility. In some examples, the biocompatible material(s) can include natural or synthetic compounds or elements including, but not limited to: metals, for example titanium or titanium alloy, or plastics such as medical grade polyvinyl chloride (PVC), polyethylene (PE), polycarbonate, or polyether ether ketone (PEEK).

Because the implantable infusion device 100 can be implanted in a patient's body, it can be desirable to reduce the overall size or dimensions of the device to minimize trauma, reduce the capability to feel the device external to the patient, and allow for the device to be implanted into smaller patients, including infants. In some instances, the implantable infusion device implantation can be limited to specific regions of the body, e.g., such as the abdomen, buttock, shoulder, skull, etc., which can further constrain the size.

In some example configurations, the reservoir 109 can also include an outlet port (or catheter port) to connect to the pumping catheter for delivery of medication to a target site (not shown). In another example, the catheter-based pumping system, e.g., as shown in FIG. 1A, can contain a refill port 116 attached to the reservoir 109 to refill the medicine or drug when it is depleted.

In the example shown in FIG. 2, implantable infusion device 100 can include a processor 103 and memory 115. The processor 103 may include, for example, one or more general-purpose microprocessors, specially designed processors, application specific integrated circuits (ASIC), field programmable gate arrays (FPGA), a collection of discrete logic, and/or any type of processing device capable of executing the techniques described in this disclosure. In some examples, the processor 103 (or any other processors described in this disclosure) can be described as a computing device. In some examples, the memory 115 can be configured to store program instructions (e.g., software instructions) that are executed by the processor 103 to carry out the processes or methods of operating and programming the implantable infusion device described in this disclosure. In other examples, the processes or methods described in this disclosure may be executed by specifically programmed circuitry of the processor 103. In some examples, the processor 103 can be configured to execute the techniques for operating and programming the implantable infusion device described in this disclosure.

The processor 103 (or any other processors described in this disclosure) can include one or more processors. The processor 103 can be connected to the memory 115, the power source 104, the piezoelectric and/or electrostrictive mechanical pumping catheter including segments 110-1 through 110-N (substantially similar to segments 16 in FIG. 1A), the communication interface 108, the alarm 107, the sensing interface 111, and the micro-energy harvesting circuitry 106.

The memory 115 can be configured to store information within the implantable infusion device during operation. The memory 115 can include a computer-readable storage medium. The memory 115, in some examples, can include a volatile memory. Examples of volatile memories include random access memories (RAM), dynamic random access memories (DRAM), static random access memories (SRAM), and any other forms of volatile memories known in the art. In some examples, the memory 115 can be used to store program instructions for execution by the processor 103.

The memory 115, in one example, can be used by software or applications running on the implantable infusion device 100 (e.g., one or more of communication interface 108, 107 and sensing interface 111) to temporarily store information during program execution. The memory 115 can be used for storing set(s) of infusion and control parameters, and/or other data, for example. This permits, as needed, infusion and control parameter adjustment to configure the implantable infusion device to operate at settings that are safe and efficacious for each individual. Different parameters may have different effects on different patients, different diseases, and even different tissue.

The power source 104 can be used to provide power to the processor 103, piezoelectric and/or electrostrictive mechanical pumping catheter including segments 110-1 through 110-N, or other components of the implantable infusion system. The power source 104 can be a primary battery, for example, a Lithium battery that once depleted will require replacement of the device. In another embodiment, power source 104 may be a rechargeable battery, such as a lithium battery or any type of rechargeable battery that may hold its charge for a period of time, depending upon the capacity of the battery, and may be recharged by a user on a regularly scheduled interval or as necessary.

In example configurations in which the power source 104 is rechargeable, the implantable infusion system can include a recharge circuit 113. The recharge circuit 113 can use an inductive coupling technique to transfer power via an electromagnetic field. In some examples, the implantable infusion catheter device 100 can includes an energy harvesting circuit 106 to receive, convert, and provide power to the power source 104. In some cases, the energy harvesting device 106 can include a bridge rectifier, a rectifier, a diode or transistor rectifier, and may include a voltage or current regulator.

The energy harvesting circuit 106 can, in some examples, can work together with, and receive power from, a RF wireless charger. For example, depending on the configuration of its electronics, antennas, and frequency ranges of operation, a RF wireless charging circuit can produce a near-field electric or magnetic field that stores energy for coupling into one or more target devices, or it can produce a far-field radiation pattern of traveling electromagnetic waves, or a combination thereof. In some examples, the energy harvesting circuity can gather energy from sources such as patient body heat, blood flow, and motion, and provide energy directly to the device or via charging of the implantable infusion system's circuitry.

The implantable infusion system 100 can use a piezoelectric and/or electrostrictive mechanical pumping catheter that can be used to pump a drug or medicine in liquid or gas form from the reservoir 109 to an outlet port of the reservoir, which can be connected to the catheter via a catheter connector to provide the drug to the patient. The pumping mechanism can include a piezoelectric-based material and/or electrostrictive-based material with two or more pumping segments that can deform independently when voltage is applied. By alternating the voltage application to the consecutive segments of the pumping mechanism, a medium (fluid or gas) can be pushed out from the reservoir through the catheter. The design provides a check valve, piezo and/or electrostrictive restriction mechanism, or other controller mechanism at the outlet port of the reservoir chamber and at the two catheter ends which used to control the flow direction.

The processor 103 can control the voltage output to each of the piezo and/or electrostrictive material segments contained within the piezoelectric and/or electrostrictive mechanical pumping catheter, e.g., segments 110-1 through 110-N. When the processor executes instructions that cause the voltage applied to the piezo and/or electrostrictive segments to be decreased, the piezo and/or electrostrictive material in one or more of the segments 110-1 through 110-N can deform, e.g., upward or downward, which can cause the fluid to be drawn into and fill the chamber, as described above with respect to FIG. 1A. As the processor controls the voltage to increase, the piezo and/or electrostrictive material can deform e.g., downward or upward, which can cause the fluid to be pushed out of the chamber and into the next chamber formed by a segment 110. The material can be deformed hundreds of times per second, thereby allowing delivery of drug from fractions of microliters over hours to thousands of microliters per hour. The processor 103 can alter the amplitude and frequency of the electronic control pattern to vary the operation of the piezoelectric and/or electrostrictive mechanical pump and hence regulate the rate of pumping and thus the amount of drug that is expelled from the reservoir 110.

The rate of pumping can be controlled by the processor/control circuitry 103 and control firmware. The downloadable programming parameters can be set via the wireless telemetry circuitry/external programmer 108.

The implantable infusion device can include a reservoir 109 that can be contained exterior to/separate from the implantable device 100. The reservoir 109 can be a basin or container that holds the medicine or drug (liquid or gas) intended for expulsion through an outlet port and catheter to a target delivery site. The reservoir 109 can have variable capacity ranging from any minimum amount measured in milliliters (mL) to hundreds of milliliters.

The reservoir 109 can be composed of one or more materials including Titanium (Ti), Stainless steel (SS), Titanium alloys e.g., TAN (Titanium-Aluminum-Niobium.), ceramics, non-degradable polymers, silicone, Kevlar®, etc. The connectors and fluid delivery pathway can be composed of flexible or rigid tubing or other pathway composed of these or other bio-suitable materials. These can be composed of, and coated in, materials including silicone, Kevlar®, and many others.

The communication interface 108 of the implantable infusion device 100 can include any type of communication network and may support wireless communication based upon any type of techniques for transferring and receiving data from a computing device. Wireless communication, for example, includes WiFi, low range telemetry, Bluetooth or inductive coupling. The external computing device used to program and communicate with the implantable device for example, can include personal computing devices, computers, servers, custom handheld devices, mobile devices, smart phones, and tablet computing devices that may program and control infusion and operational parameters of the implantable infusion device.

Implantable infusion device 100 can also include an alarm 107 and a sensing interface 111 to detect, for example, the level of medicine or drug (liquid or gas) present in the reservoir, the piezoelectric and/or electrostrictive mechanical pumping flow rate, the capacity and current level of the power source, catheter or drug delivery path occlusion, or status of the re-charge and energy harvesting circuits. The alarm 107 and the sensing interface 111 can activate audible or tactical (e.g., vibration) alerts when operational parameters are at or below programmed thresholds, device component failures occur, etc.

The implantable device 100 can also contain positional and motion (inertial, magnetic, etc.) sensing device(s) (e.g., single or combination of accelerometer, gyroscope, or other motion and 3D sensing devices) capable of sensing user position, motion, etc. as part of the alarm 107 and sensing interface/circuitry 111. Utilizing a 3D sensing system, the device 100 can determine geo location information including user orientation data (e.g., roll, pitch, and yaw) and user location tracking (x, y, z), and store this data in the device's resident memory. This data can be used to track user activity, to determine gain/loss in mobility, increase/decrease in user activity over time, and other variances and/or changes of physiological related behavior.

One or more sensors (not depicted in FIG. 2) can also be incorporated for sensing aspects of the patient including, but not limited to, reservoir level, blood sugar, heart rate, blood pressure, blood oxygenation, motion (roll, pitch, yaw, x, y, x, speed, etc.) sensors including but not limited to GPS, gyro, rate, rotational, and body temperature. These sensors can work together with the one or more of the components in FIG. 2 to provide full sensing, tracking, and storage of current and historical physiological data. The historical data can be utilized to gather and generate and interpret trending of the user data over time. In this manner, the device 100 can acquire data from one or more sensors via the sensor interface 111, store data in the memory 115 representing the data, and in some examples, modify an operating parameter of the device, e.g., pump speed, using the stored data. In some examples, the device can use the trend information to modifying an operating parameter of the device.

In some example implementations, the device 100 can transmit, e.g., via the wireless telemetry circuitry and communication interface 108, sensor data acquired by the one or more sensors, e.g., raw sensor data, and/or processed sensor data, e.g., analyzed and/or processed by processor 103, to one or more wearable devices, e.g., activity trackers. In this manner, a user with a wearable device can receive important information about the infusion device 100 and/or the user. For example, information about the amount of medicine, e.g., insulin, in the reservoir based on reservoir level sensor data can be transmitted to the user along with the user's blood sugar level based on data from a sensor in communication with the user's blood.

The processor 103, the memory 115, the alarm 107 and the sensing interface 111 can be used together or in combinations to support algorithms that can detect critical changes of the system or user activity/physiology to triggers to notify the user or physicians of important changes that require user or physician intervention. Different parameters may have different effects on different patients, different diseases, and even different tissue. This data can be gathered by the device and analyzed by the device itself dynamically or archived for later download and analyzing by an external device, e.g., via telemetry circuitry 108. The device can have local on-board processing and programming support for improving its own operation and support to the patient by analyzing this trend data.

Figure 3A:
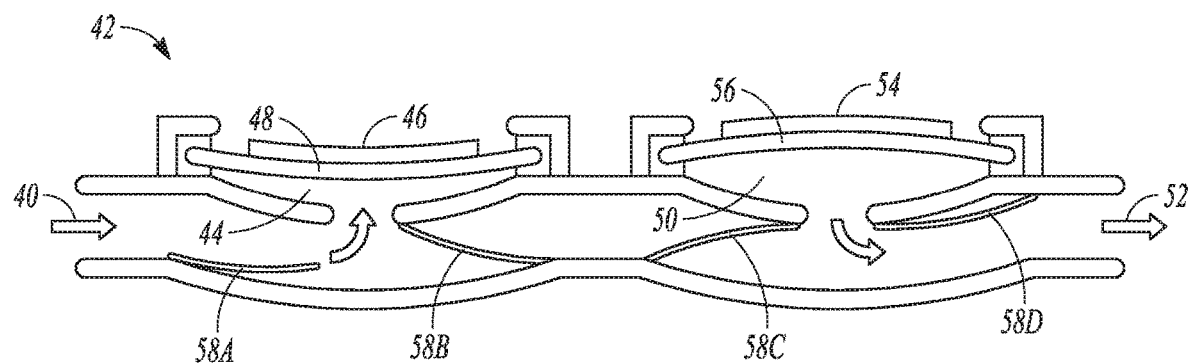
FIGS. 3A-3B are conceptual diagrams illustrating an example of a piezoelectric and/or electrostrictive pump that can be used to implement various techniques of this disclosure.
Figure 3B:
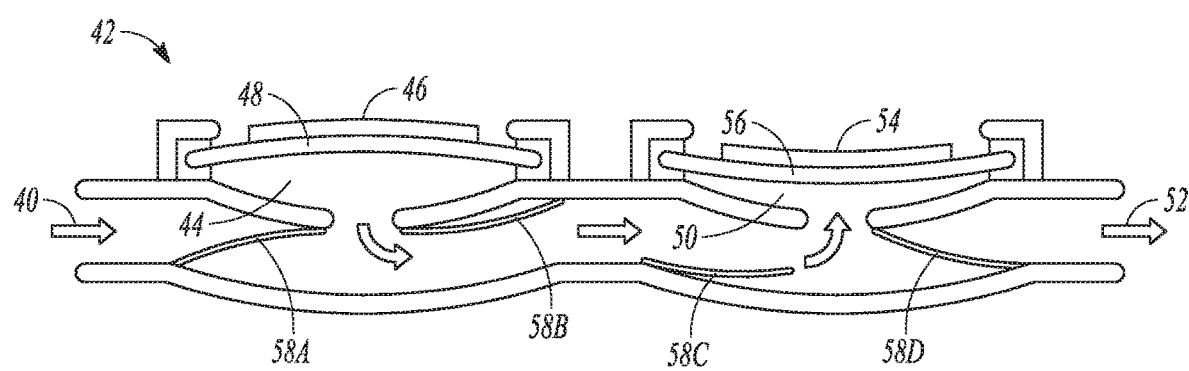

FIGS. 3A-3B are conceptual diagrams illustrating an example of a piezoelectric and/or electrostrictive pumping mechanism that can be used to implement various techniques of this disclosure. One example pump that can be used is the Bartels "mp5" or "mp6" micropump manufactured by Bartels Mikrotechnik GmbH. FIGS. 3A-3B depict a pumping process that causes intake of a fluid from an internal or external reservoir (not depicted) through an inlet port 40 of a pump 42 and into a first chamber 44 by application of a voltage to an electrode/contact 46 connected to a flexible piezo and/or electrostrictive material 48 engaged to the first chamber 44. Fluid in the second chamber 50 is forced out the outlet port 52 by application of a voltage to an electrode/contact 54 connected to a flexible piezo and/or electrostrictive material 56 engaged to the second chamber 50. The pump 42 includes valves 58A-D that can open/close in a coordinated manner with the chambers 44, 50 to allow fluid to be pumped from the inlet port 40 to the outlet port 52 of each chamber and to the target site. A check valve can be between each of these pumps in order to control and restrict backflow between the pumps and segments, FIG. 4 is a schematic diagram illustrating an example implantable infusion system that can utilize various piezoelectric and/or electrostrictive pumping techniques, in accordance with this disclosure. The system of FIG. 4 can utilize the pumping catheter 10 shown in FIGS. 1A-1C that includes deformable segments 16A-16F. The system of FIG. 4 can include a piezoelectric and/or electrostrictive pressure pump master 60 (similar to pump 42 in FIGS. 3A and 3B) in communication with a first, e.g., unpressurized, reservoir 62 and a second, e.g., pressurized, reservoir 64. The piezo and/or electrostrictive pressure pump master 60 and the pressurized reservoir 64 can help ensure that fluid from the reservoir reaches the pumping catheter 10. In some example configurations, neither reservoir 62 nor 64 is pressurized, however.

The pump master 60 can be in communication with a power source and control electronics 20, which are described above with respect to FIG. 2. Other configurations can include another piezo and/or electrostrictive pressure pump at the outlet of the reservoir 64, for example.

The first reservoir 62 can include a first refill port 68 that is in communication with a remote second refill port 70 to allow a clinician, for example, to refill the medicament in the reservoir 62. The second reservoir 64 can include an outlet port 72 in communication with a catheter 74 that includes a piezoelectric and/or electrostrictive pumping catheter 10. In some examples, the catheter 74 can further include a flow control valve 78, e.g., a check valve, placed proximal to the piezoelectric and/or electrostrictive pumping catheter 10, or with a plurality of check valves, e.g., one for each pumping segment. In some example configurations, a check valve can be placed between each of the pumping segments to further control any backflow between these segments.

As described above, the implantable infusion system of FIG. 4 can utilize the pumping catheter 10 of FIGS. 1A-1C, which can include one or more deformable segments 16. In other configurations, such as described below with respect to FIGS. 5 and 6, example implantable infusions systems can alternative pumping catheter designs.

Figure 4:
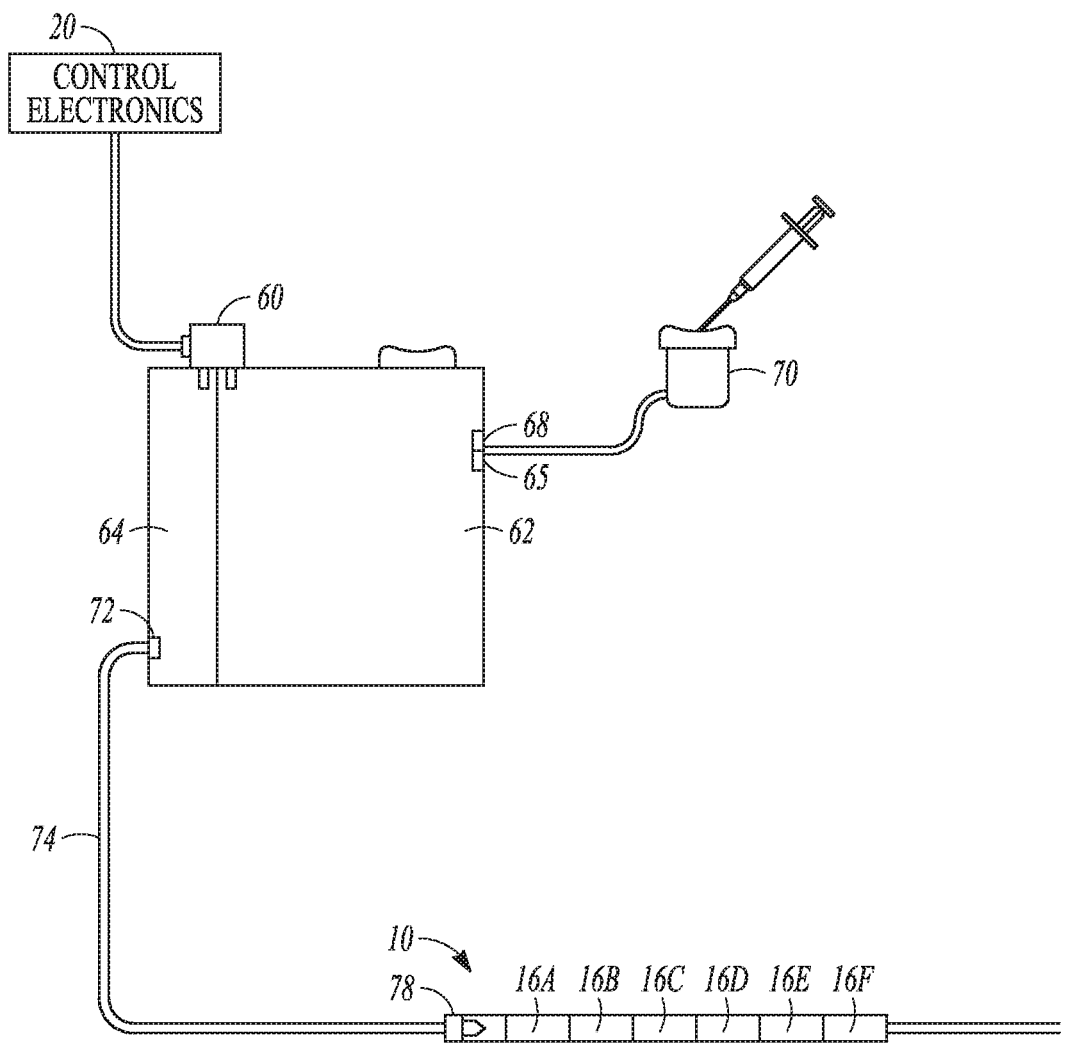
FIG. 4 is a schematic diagram illustrating an example implantable infusion system that can utilize various piezoelectric and/or electrostrictive pumping techniques, in accordance with this disclosure.
Figure 5:
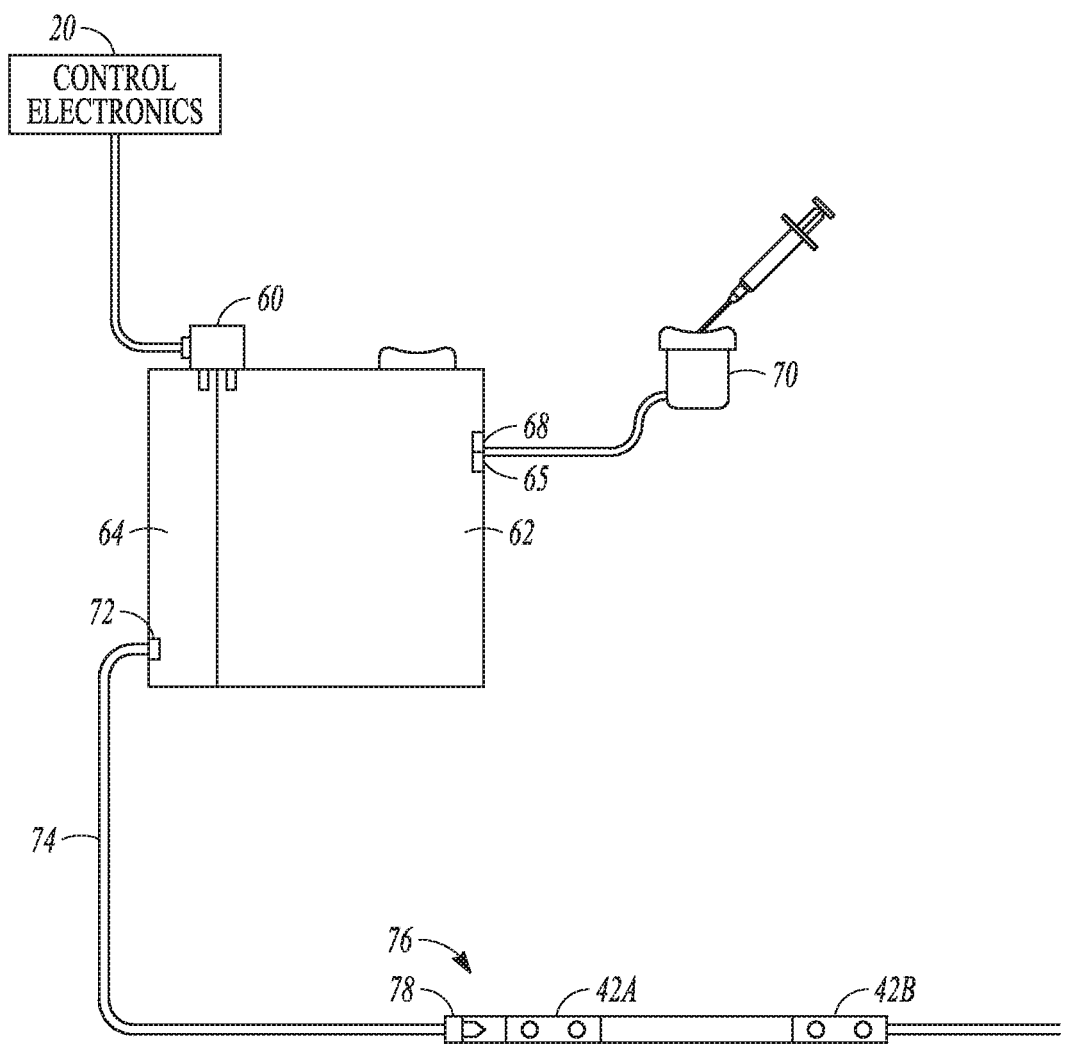
FIG. 5 is a schematic diagram illustrating another example implantable infusion system that can utilize various piezoelectric and/or electrostrictive pumping techniques, in accordance with this disclosure.

FIG. 5 is a schematic diagram illustrating another example implantable infusion system that can utilize various piezoelectric and/or electrostrictive pumping techniques, in accordance with this disclosure. Many of the components of the system of FIG. 5 are similar to those described above with respect to FIG. 4. The system of FIG. 5 can include a piezoelectric and/or electrostrictive pressure pump master 60 in communication with a first, e.g., unpressurized, reservoir 62 and a second, e.g., pressurized, reservoir 64. The piezo and/or electrostrictive pressure pump master 60 and the pressurized reservoir 64 can help ensure that fluid from the reservoir reaches the first pump in the catheter, e.g., piezo and/or electrostrictive slave 42A in FIG. 5 (similar to pump 42 in FIGS. 3A and 3B). In some example configurations, neither reservoir 62 nor 64 is pressurized, however.

The pump master 60 can be in communication with a power source and control electronics 20. Other configurations can include another piezo and/or electrostrictive pressure pump at the outlet of the reservoir 64, for example.

The first reservoir 62 can include a first refill port 68 that is in communication with a remote second refill port 70 to allow a clinician, for example, to refill the medicament in the reservoir 62. The second reservoir 64 can include an outlet port 72 in communication with a catheter 74 that includes a piezoelectric and/or electrostrictive pumping catheter system 76, which is different than the pumping catheter 10 described with respect to FIG. 4.

In addition to the master piezoelectric and/or electrostrictive pump 60, the system of FIG. 5 can include a catheter 74 that includes first and second piezoelectric and/or electrostrictive pumps 42A, 42B (similar to pump 42 in FIGS. 3A and 3B), e.g., piezo and/or electrostrictive slaves in FIG. 5, and a flow control valve 78, e.g., a check valve, placed proximal to the first piezoelectric and/or electrostrictive pump 42A, or with a plurality of check valves, on for each pumping segment or pumps. An example piezoelectric and/or electrostrictive pump 42 is shown and described in FIGS. 3A and 3B. The first and second piezoelectric and/or electrostrictive pumps 42A, 42B, e.g., piezo and/or electrostrictive slaves in FIG. 5, can be spaced apart from one another along a length of the catheter.

Figure 6:
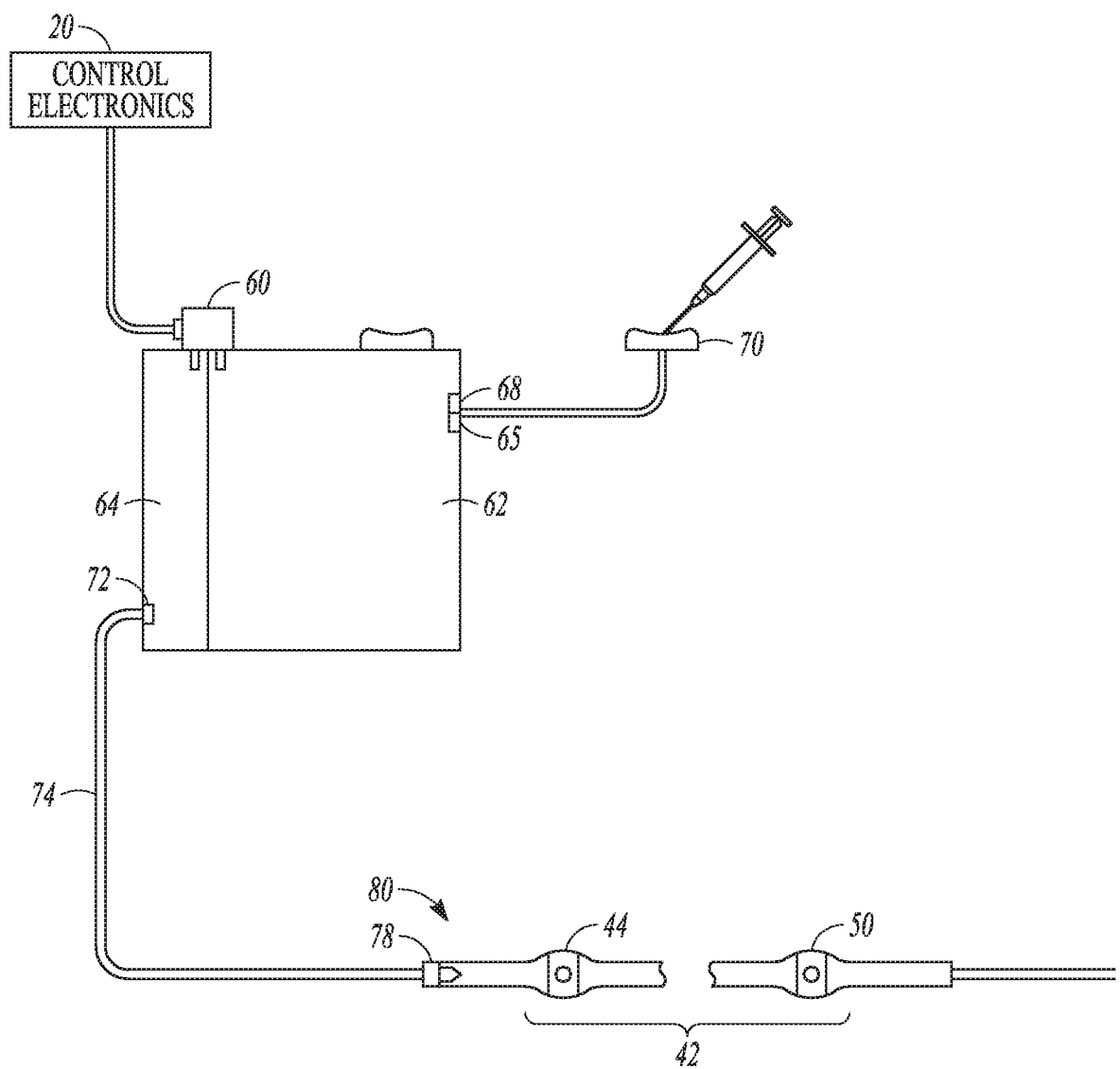
FIG. 6 is a schematic diagram illustrating another example implantable infusion system that can utilize various piezoelectric and/or electrostrictive pumping techniques, in accordance with this disclosure.

FIG. 6 is a schematic diagram illustrating another example implantable infusion system that can utilize various piezoelectric and/or electrostrictive pumping techniques, in accordance with this disclosure. The system of FIG. 6 can include a piezoelectric and/or electrostrictive pressure pump 60 in communication with a first, e.g., unpressurized, chamber or reservoir 62 and a second, e.g., pressurized, reservoir 64. The pump can be in communication with a power source and control electronics 20.

The first reservoir 62 can include a first refill port 68 that can be in communication with a remote second refill port 70 to allow a clinician, for example, to refill the medicament in the reservoir 62. The first reservoir 62 can additionally or alternatively include a programmable on/off illuminated refill port 65. Such a refill port 65 can be illuminated using materials including but not limited to one or more light emitting diodes (LEDs), light pipe material, electro-luminescent material, or a series of LED lights. The second, pressurized reservoir 64 can include an outlet port 72 in communication with a catheter (or catheter port) that includes a piezoelectric and/or electrostrictive catheter system. In some example implementations, the catheter port 72 can be illuminated as described above.

In contrast to the pumping catheter 76 of FIG. 5, which can include first and second piezoelectric and/or electrostrictive pumps 42A, 42B in the catheter 74, the example catheter 74 shown in FIG. 6 can include a pumping catheter 80 that can include a single piezoelectric and/or electrostrictive pump 42, such as shown in FIGS. 3A and 3B, positioned within the catheter 74. As depicted in FIG. 6, the two chambers 44, 50 of the piezo and/or electrostrictive pump 42 can be separated from one another by a distance, e.g., 1 centimeter to a number N centimeters.

The single catheter pump design of FIG. 6 can be thinner than the design described above with respect to FIG. 5, which can be advantageous for implantation within a patient's skull, for example. In addition, the control of the single catheter pump design of FIG. 6 can be simpler than the design of FIG. 5 because there is only one opening and one closing mechanism in the catheter 74 to be controlled by a processor.

Figure 7:
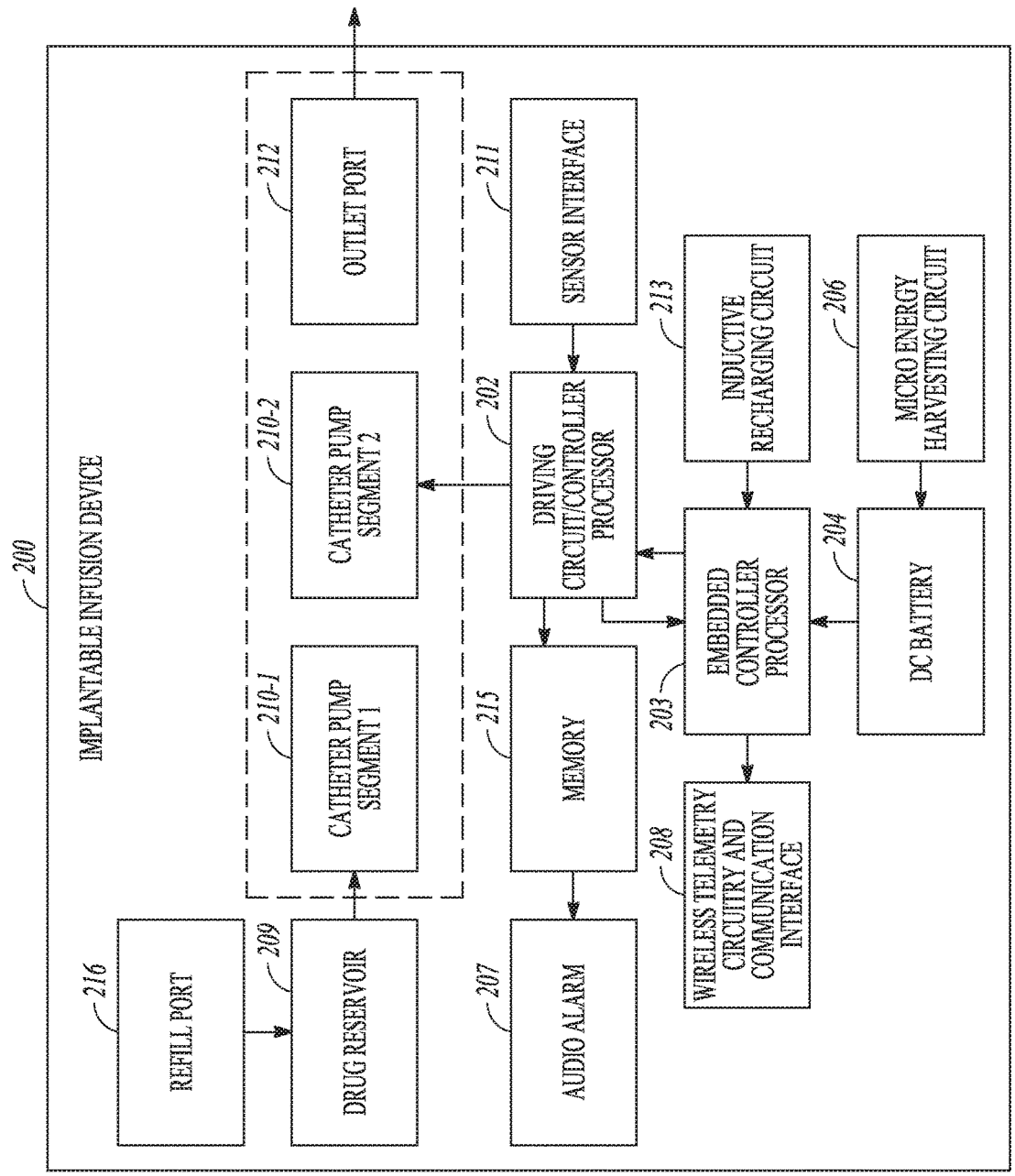
FIG. 7 illustrates a block diagram of another example of an implantable infusion device.

FIG. 7 illustrates a block diagram of another example of an implantable infusion device 200. The device 200 of FIG. 7 can utilize a piezoelectric and/or electrostrictive mechanical pumping catheter that includes one or more miniature piezo and/or electrostrictive pumping devices contained within the catheter and connected to an external reservoir, such as shown in FIGS. 5 and 6. The implantable infusion device 200 can include a first processor 203, e.g., an embedded controller/processor, to control power and communication functionality associated with a power source 204, a recharge circuit 213, an energy harvesting circuit 224, and a communication interface 208.

The implantable infusion device 200 can further include a second processor 202 to control and/or be in communication with a piezoelectric and/or electrostrictive mechanical pumping catheter 210, such as the pumping catheters 78 or 80 of FIGS. 5 and 6, a reservoir 209, an alarm 207, and a sensing interface 211, configured to receive information from one or more sensors, including biological sensors. The implantable infusion device 200 can include one or more of the storage devices, communication and alarm, sensing interfaces, power sources, piezoelectric and/or electrostrictive mechanical pumps, reservoirs, and recharge and energy harvesting circuits.

The pumping catheter 210 can be made from a biocompatible material or uniformly coated with a biocompatible material to attain a specified biocompatibility. In some examples, the biocompatible materials include natural or synthetic compounds or elements including, but not limited to: metals, for example titanium or titanium alloy, or plastics such as medical grade polyvinyl chloride (PVC), polyethylene (PE), polycarbonate, or polyether ether ketone (PEEK). Because the implantable infusion device 200 can be implanted in a patient's body, it can be desirable to reduce the overall size or dimensions of the housing of the device to minimize trauma and reduce the capability to feel the device external to the patient. In some instances, implantable infusion device implantation can be directed to specific regions of the body such as the abdomen, which further constrains the size. Existing implantable infusion devices can be bulky due to the components that are contained within the housing.

The reservoir 209 can also contain an outlet port to connect to a catheter for delivery medication to a target site (not shown). In another example, the housing of the device 200 may contain an inlet port attached to the reservoir 209 to refill the medicine or drug when it is depleted.

In the example of FIG. 7, the implantable infusion device 200 can include a memory 215. The processor 203 and the memory 215 can be similar to the processor 103 and the memory 115 described above with respect to FIG. 2 and, for purposes of conciseness, will not be described in detail again. The processor 203 can be connected to the memory 215, the power source 204, the piezoelectric and/or electrostrictive mechanical pump 210, the communication interface 208, the alarm 207, and the sensing interface 211.

The power source 204 can be used to provide power to the processor 203, the piezoelectric and/or electrostrictive mechanical pumping catheter 210, or other components of implantable infusion device 200. The power source 204 can be similar to the power source 104 described above with respect to FIG. 2 and, for purposes of conciseness, will not be described in detail again. In an example configuration, the power source 204 can be rechargeable and the implantable infusion device 200 can include a recharge circuit 213, e.g., utilizing inductive coupling techniques to transfer power via an electromagnetic field. In some embodiments, implantable infusion device 200 includes an energy harvesting circuit 206 to receive, convert, and provide power to the power source 204, similar to the circuit 106 described above with respect to FIG. 2.

The implantable infusion device 200 can include a piezoelectric and/or electrostrictive mechanical pumping catheter that can include a first pump 210-1 (e.g., a single pump 42 of FIGS. 3A and 3B as described with respect to FIG. 6) and, in some examples, a second pump 210-2 (e.g., two pumps 42 as described with respect to FIG. 5) that can be used to pump a drug or medicine in liquid or gas form from the reservoir 209 to the outlet port 212 and into and through the catheter to provide the drug to the patient, as shown in FIGS. 5 and 6.

The pumping catheter mechanism can include a series of self-contained micro piezo-based and/or electrostrictive-based mechanisms that each work together to pump fluid through the catheter. By actuating the voltage application to each pump contained in the catheter mechanism, and alternating pumping (opening/closing) of each consecutive pump housed in the catheter in a controlled sequence, a medium (fluid or gas) can be pushed out from the chamber through the piezo and/or electrostrictive pumps/catheter body. Multiples of these can be controlled by the processing circuitry to control rate and flow, e.g., voluntary peristaltic flow, of the fluid from the reservoir through the catheter.

As shown in FIGS. 4-6, the system can include a check valve or piezo and/or electrostrictive compression mechanism on one side of the catheter to control the flow direction. In some example configurations, the system can include a check valve or piezo and/or electrostrictive compression mechanism on both sides of the catheter. The processor 203 can control a voltage output to each piezoelectric and/or electrostrictive mechanical pump housed in the catheter e.g., pumps 210-1 and 210-2. As the voltage is applied to each piezo and/or electrostrictive pump in the catheter, the specific pump is actuated to pump, causing the fluid/gas to be drawn into and filling that particular pump. As the voltage is increased, the deformation of the piezo and/or electrostrictive material of the pump can cause the fluid to be pushed out of that particular pump in the catheter and into the adjacent segment of the catheter. While the previous piezo and/or electrostrictive pump in the catheter remains closed, the next pump in sequence can receive the fluid/gas pushed into that pump from the previous one. That pump ($3^{rd}$ in this sequence) is then triggered, which continues to force the fluid along the direction of flow. As the sequence of action continues forward down the catheter pumps, the last one closed in the sequence can be opened (voltage removed), allowing the fluid to exit the catheter and be delivered to the target site. The pumps can each be fired hundreds of times in a second. The processor 203 may alter the amplitude and frequency of the electronic control pattern to vary the operation of the piezoelectric and/or electrostrictive mechanical pump and hence regulate the amount and rate of drug that is expelled from the reservoir 209.

The implantable infusion device 200 can include a reservoir 209. The reservoir can include a container that holds the medicine or drug (liquid or gas) intended for expulsion through an outlet port and non-pumping catheter to a target delivery site. Reservoir 209 may have variable capacity—example ranges can include about 20 mL, about 40 mL, about 60 mL, etc.

The communication interface 208 of the implantable infusion device 200 can be similar to the communication interface 108 described above. Implantable infusion device 200 may also include an alarm 207 and sensing interface 211 to detect, for example, the level of medicine or drug (liquid or gas) present in the reservoir, the piezoelectric and/or electrostrictive mechanical pump flow rate, the capacity of the power source, catheter or drug delivery path occlusion, or status of the recharge and energy harvesting circuits. The alarm 207 and sensing interface 211 may activate an audible or tactical (i.e., vibration) alerts when operational parameters are at or below programmed thresholds. Sensors may include pressure, etc.

The refill port 216 can incorporate an electronic coil or other sensing circuitry to determine when a needle is inserted into the port to assist the clinician during refill (to avoid accidental injection into the body rather than into the reservoir. A handheld device can be provided to sense the coil surrounding the refill port in order to locate the refill port and facilitate accurate insertion of the refill needle for injection of drug to refill the infusion device.

The refill port 216 can be positioned in an easily accessible location on the external surface of the implantable device's reservoir or can be packaged in a separate remotely positioned location. The port can provide a mechanism that resists microbial entry into the implantable device/reservoir/drug.

FIGS. 8A-8E depict conceptual diagrams illustrating an example pumping sequence of an example piezoelectric and/or electrostrictive pumping catheter, in accordance with this disclosure. The example portion of a catheter 300 of FIGS. 8A-8E can be similar to the catheter 10 described above with respect to FIGS. 1A-1C. For simplicity, the example catheter 300 depicted includes four segments 16, namely segments 16A-16D, and can utilize a right-to-left closing sequence beginning with segment 16A and ending with segment 16D.

Figure 8A:
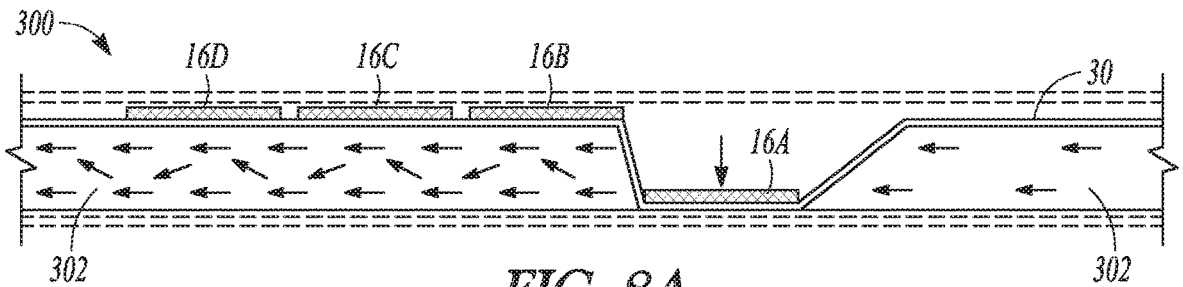
FIGS. 8A-8E depict conceptual diagrams illustrating a pumping sequence of an example piezoelectric and/or electrostrictive pumping catheter, in accordance with this disclosure.

As seen in FIG. 8A, a processor, e.g., processor 103 of FIG. 2, can control the segment 16A to close, and the processor 103 can control segments 16B-16D to remain open. A cross-sectional view of such a configuration was described above with respect to FIG. 1D.

Figure 8B:
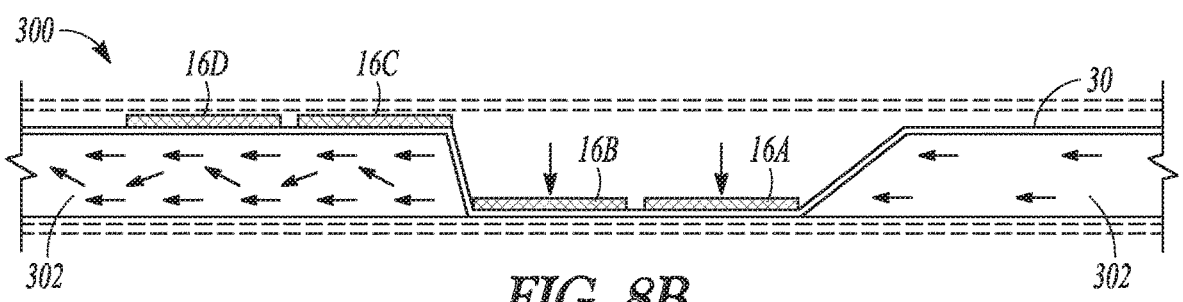

In FIG. 8B, the processor can control the segment 16B to close, which can force the fluid 302 further along a length of the catheter 300. As seen in FIG. 8B, the segment 16A can remain closed and the segments 16B-16D can remain open.

Figure 8C:
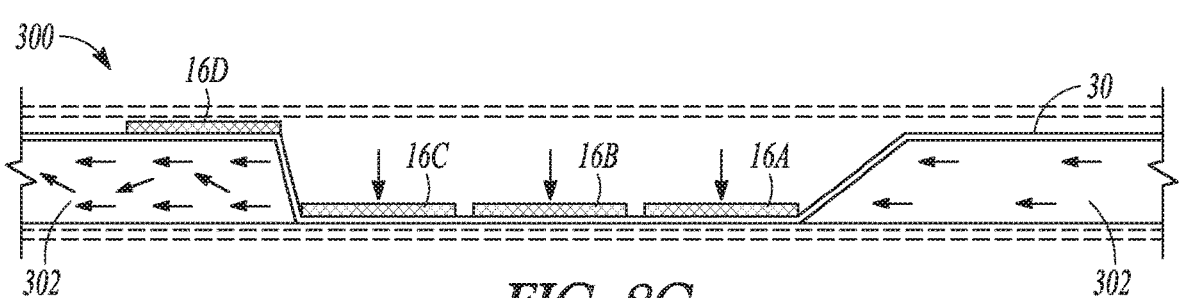

In FIG. 8C, the processor can control the segment 16C to close, which can force the fluid 302 further along a length of the catheter 300. As seen in FIG. 8C, the segments 16A, 16B can remain closed and the segments 16D can remain open.

Figure 8D:
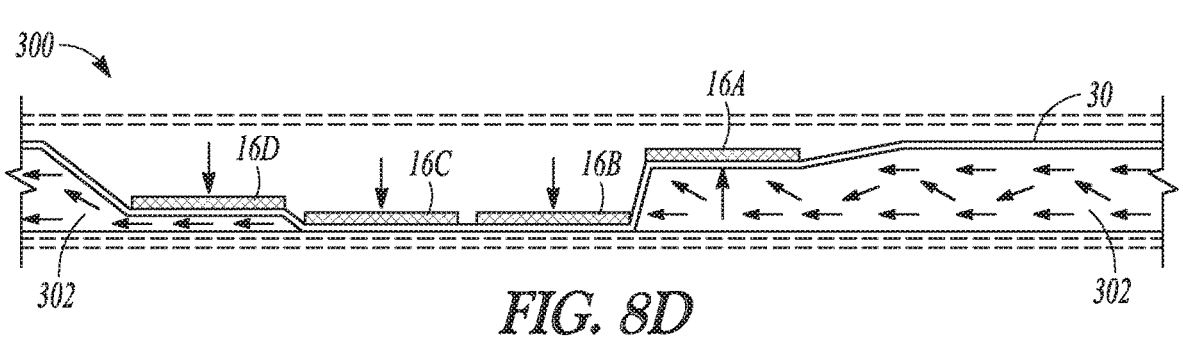

In FIG. 8D, the processor can control the last segment 16D to close (shown during a transition between an open state and a closed state), which can force the fluid 302 further along a length of the catheter 300. In addition, the processor can control the segment 16A to open (shown during a transition between a closed state and an open state), which can draw the fluid 302 into the catheter 300. The segments 16B, 16C can remain closed to prevent backflow.

Figure 8E:
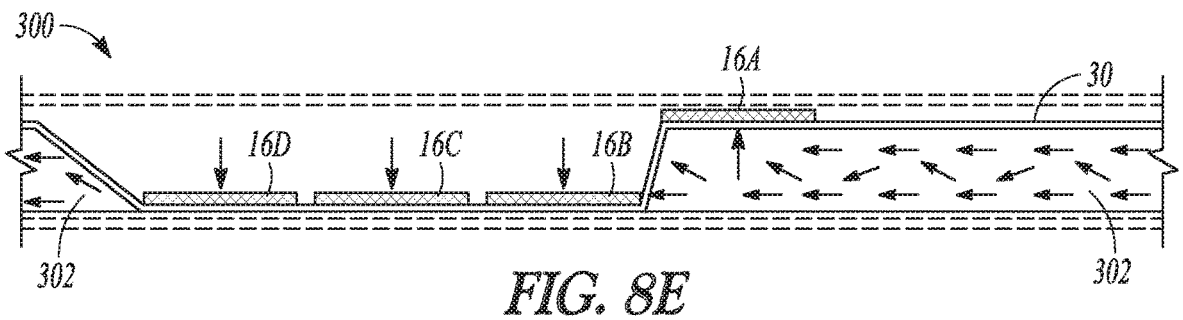

Finally, FIG. 8E depicts the segments 16A and 16D of FIG. 8D fully transitioned to an open state and a closed state, respectively, with segments 16B, 16D closed. The pumping sequence of FIGS. 8A-8E, or another pumping sequence, can be repeated in order to pump the fluid 302 through the catheter.

VARIOUS NOTES AND EXAMPLES

Example 1 can include or use subject matter (e.g., a system, apparatus, method, article, or the like) that can include or use a pumping catheter comprising a tubular member defining a lumen, the tubular member having a proximal end, a distal end, and a plurality of deformable segments extending therebetween; and at least one pump positioned in at least one of the plurality of deformable segments, wherein the at least one pump is configured to receive a control signal and, in response, controllably deform at least one segment to control at least one of a rate of fluid flow through the lumen and a volume of fluid through the lumen.

In Example 2, the subject matter of Example 1 may optionally include wherein the at least one pump comprises a first pump and a second pump, wherein the first pump is positioned in a first segment and the pump is positioned in a second segment.

In Example 3, the subject matter of one or more of Examples 1 to 2 may optionally include a first check valve positioned proximal to the pump.

In Example 4, the subject matter of one or more of Examples 1 to 3 may optionally include a second check valve positioned distal to the at least one pump.

In Example 5, the subject matter of one or more of Examples 1 to 4 may optionally include an implantable infusion device.

In Example 6, the subject matter of Example 5 may optionally include wherein the at least one pump includes at least one pump, and wherein the implantable infusion device comprises at least one piezoelectric and/or electrostrictive pump.

In Example 7, the subject matter of Example 5 may optionally include at least one sensor selected from the group consisting of pressure, positional, motion, locational, and biological sensors.

In Example 8, the subject matter of one or more of Examples 1 to 7 may optionally include, wherein the tubular member includes an outer member and an inner member, and wherein the inner member includes the plurality of segments and the at least one piezoelectric and/or electrostrictive pump.

In Example 9, the subject matter of one or more of Examples 1 to 8 may optionally include, wherein the at least one pump includes at least one of a piezoelectric material and an electrostrictive material.

In Example 10, the subject matter of one or more of Examples 1 to 9 may optionally include, wherein the at least one pump includes a shape-memory alloy.

Example 11 can include or use subject matter (e.g., a system, apparatus, method, article, or the like) that can include or use an implantable infusion device comprising a reservoir configured to retain a fluid to be dispensed within a patient; at least one piezoelectric and/or electrostrictive mechanical pumping catheter for dispensing the fluid contained within the reservoir; a transceiver; and a processor to control operation of the piezoelectric and/or electrostrictive mechanical pumping catheter.

In Example 12, the subject matter of Example 11 optionally include, wherein the piezoelectric and/or electrostrictive mechanical pumping catheter includes a pumping catheter including at least two deformable segments, wherein the at least two deformable segments include at least two piezoelectric and/or electrostrictive pumps configured to receive a control signal and, in response, controllably deform to control a fluid flow through a lumen of the catheter.

In Example 13, the subject matter of one or more of Examples 11 to 12 may optionally include, wherein the piezoelectric and/or electrostrictive mechanical pumping catheter includes a sensor, and wherein the processor is configured to determine pumping efficacy and to detect occlusions in the pumping catheter using data received from the sensor.

In Example 14 the subject matter of one or more of Examples 11 to 13 may optionally include, wherein the piezoelectric and/or electrostrictive mechanical pumping catheter system includes an energy harvesting circuitry configured to gather and provide energy to the implantable device and circuitry.

In Example 15, the subject matter of one or more of Examples 11 to 14 may optionally include, wherein the piezoelectric and/or electrostrictive mechanical pumping catheter includes a catheter including at least two piezoelectric and/or electrostrictive pumps.

In Example 16, the subject matter of one or more of Examples 11 to 15 may optionally include, wherein the piezoelectric and/or electrostrictive mechanical pumping catheter includes a plurality of piezoelectric and/or electrostrictive pumps along a length of an interior of the pumping catheter.

In Example 17, the subject matter of one or more of Examples 11 to 16 may optionally include, wherein the at least one piezoelectric and/or electrostrictive mechanical pumping catheter includes two or more piezoelectric and/or electrostrictive mechanical pumping catheters.

In Example 18, the subject matter of one or more of Examples 11 to 17 may optionally include, wherein the processor is configured to communicate wirelessly with the piezoelectric and/or electrostrictive mechanical pumping catheter using the transceiver.

In Example 19, the subject matter of one or more of Examples 11 to 18 may optionally include, a memory device, wherein the processor is configured to acquire data corresponding to at least one characteristic of the pumping catheter from at least one sensor, and wherein the processor is configured to store at least some of the acquired data in the memory device.

In Example 20, the subject matter of one or more of Examples 11 to 19 may optionally include, wherein the processor is configured to analyze at least some of the acquired data and, using the analyzed data, perform at least one of the following modify an operating parameter of the device; and store data in the memory device representing trend information of the device.

In Example 21, the subject matter of one or more of Examples 11 to 20 may optionally include, wherein the transceiver is configured to transmit at least some of the stored data to an external processor for analysis.

In Example 22 the subject matter of one or more of Examples 11 to 21 may optionally include, wherein the processor is configured to: analyze at least some of the acquired data to generate trend information of the device; store data in the memory device representing the trend information; and using the stored data, modify an operating parameter of the device.

In Example 23, the subject matter of one or more of Examples 11 to 22 may optionally include at least one of a refill port configured to be illuminated and a catheter port configured to be illuminated to provide visibility through a patient's skin when implanted.

In Example 24, the subject matter of one or more of Examples 11 to 23 may optionally include, wherein the processor is configured to generate an alarm signal to indicate at least one of the following conditions: a low battery, a pumping catheter occlusion, and a low reservoir level utilizing data from one or more sensors.

In Example 25, the subject matter of one or more of Examples 11 to 24 may optionally include, wherein the transceiver is configured to wirelessly transmit pumping catheter data selected from the group consisting of the following: at least one programming parameter, a drug volume level, and sensor data.

Each of these non-limiting examples may stand on its own, or may be combined in various permutations or combinations with one or more of the other examples.

The above detailed description includes references to the accompanying drawings, which form a part of the detailed description. The drawings show, by way of illustration, specific embodiments in which the invention may be practiced. These embodiments are also referred to herein as "examples." Such examples may include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein may be machine or computer-implemented at least in part. Some examples may include a computer-readable medium or machine-readable medium encoded with instructions operable to configure an electronic device to perform methods as described in the above examples. An implementation of such methods may include code, such as microcode, assembly language code, a higher-level language code, or the like. Such code may include computer readable instructions for performing various methods. The code may form portions of computer program products. Further, in an example, the code may be tangibly stored on one or more volatile, non-transitory, or non-volatile tangible computer-readable media, such as during execution or at other times. Examples of these tangible computer-readable media may include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments may be used, such as by one of ordinary skill in the art upon reviewing the above description. The Abstract is provided to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments may be combined with each other in various combinations or permutations. The scope of the invention should be determined with reference to the appended claims, along with the full scope of equivalents to which such claims are entitled.

The invention claimed is:

1. A pumping catheter comprising:
   a tubular member defining a lumen, the tubular member having an outer tubular member, an inner tubular member, a proximal end, a distal end, and a plurality of deformable segments extending therebetween; and
   at least one pump positioned in at least one of the plurality of deformable segments, wherein the at least one pump includes one or more of a piezoelectric or an electrostrictive pump, and the at least one pump is disposed on the inner tubular member and between the outer tubular member and the inner tubular member so that the at least one pump deforms part of the inner tubular member during pumping,
   wherein the at least one pump is configured to receive a control signal and, in response, controllably deform at least one segment of the plurality of deformable segments to control at least one of a rate of fluid flow through the lumen and a volume of fluid through the lumen.

2. The pumping catheter of claim 1, wherein the at least one pump comprises a first pump and a second pump, wherein the first pump is positioned in a first segment of the plurality of deformable segments and the second pump is positioned in a second segment of the plurality of deformable segments.

3. The pumping catheter of claim 1, comprising:
   a first check valve positioned proximal to the at least one pump.

4. The pumping catheter of claim 3, comprising:
   a second check valve positioned distal to the at least one pump.

5. The pumping catheter of claim 1, wherein the at least one pump includes at least one of a piezoelectric material and an electrostrictive material.

6. The pumping catheter of claim 1, wherein the at least one pump includes a shape-memory alloy.

7. A system comprising:
   the pumping catheter of claim 1 in combination with an implantable infusion device.

8. The system of claim 7, comprising: at least one sensor selected from the group consisting of pressure, positional, motion, locational, and biological sensors.

9. An implantable infusion device, comprising:
   a reservoir configured to retain a fluid to be dispensed within a patient;
   at least one piezoelectric and/or electrostrictive mechanical pumping catheter for dispensing the fluid contained within the reservoir, wherein the at least one piezoelectric and/or electrostrictive mechanical pumping catheter includes:
   a tubular member defining a lumen, the tubular member having an outer tubular member, an inner tubular member, a proximal end, a distal end, and a plurality of deformable segments extending therebetween; and at least one pump positioned in at least one of the plurality of deformable segments, wherein the at least one pump includes one or more of a piezoelectric or an electrostrictive pump, and the at least one pump is disposed on the inner tubular member and between the outer tubular member and the inner tubular member so that the at least one pump deforms part of the inner tubular member during pumping, wherein the at least one pump is configured to receive a control signal and, in response, controllably deform at least one segment of the plurality of deformable segments to control at least one of a rate of fluid flow through the lumen and a volume of fluid through the lumen;

a transceiver; and a processor to control operation of the at least one piezoelectric and/or electrostrictive mechanical pumping catheter.

10. The implantable infusion device of claim 9, wherein the at least one piezoelectric and/or electrostrictive mechanical pumping catheter includes a pumping catheter including at least two deformable segments, wherein each of the at least two deformable segments include the at least one piezoelectric and/or electrostrictive pump configured to receive a control signal and, in response, controllably deform to control a fluid flow through a lumen of the catheter.

11. The implantable infusion device of claim 9, wherein the at least one piezoelectric and/or electrostrictive mechanical pumping catheter includes a sensor, and wherein the processor is configured to determine pumping efficacy and to detect occlusions in the at least one piezoelectric and/or electrostrictive mechanical pumping catheter using data received from the sensor.

12. The implantable infusion device of claim 9, wherein the at least one piezoelectric and/or electrostrictive mechanical pumping catheter includes an energy harvesting circuitry configured to gather and provide energy to the implantable infusion device and the energy harvesting circuitry.

13. The implantable infusion device of claim 9, wherein the at least one piezoelectric and/or electrostrictive mechanical pumping catheter includes two or more piezoelectric and/or electrostrictive mechanical pumping catheters.

14. The implantable infusion device of claim 9, wherein the processor is configured to communicate wirelessly with the at least one piezoelectric and/or electrostrictive mechanical pumping catheter using the transceiver.

15. The implantable infusion device of claim 9, further comprising:

a memory device, wherein the processor is configured to acquire data corresponding to at least one characteristic of the at least one piezoelectric and/or electrostrictive mechanical pumping catheter from at least one sensor, and wherein the processor is configured to store at least some of the acquired data in the memory device.

16. The implantable infusion device of claim 15, wherein the processor is configured to analyze at least some of the acquired data and, using the analyzed data, perform at least one of the following:

modify an operating parameter of the implantable infusion device; and store data in the memory device representing trend information of the implantable infusion device.

17. The implantable infusion device of claim 15, wherein the transceiver is configured to transmit at least some of the stored data to an external processor for analysis.

18. The implantable infusion device of claim 15, wherein the processor is configured to:

analyze at least some of the acquired data to generate trend information of the implantable infusion device;

store data in the memory device representing the trend information; and using the stored data, modify an operating parameter of the implantable infusion device.

19. The implantable infusion device of claim 9, comprising at least one of a refill port configured to be illuminated and a catheter port configured to be illuminated to provide visibility through a patient's skin when implanted.

20. The implantable infusion device of claim 9, wherein the processor is configured to generate an alarm signal to indicate at least one of the following conditions: a low battery, a pumping catheter occlusion, and a low reservoir level utilizing data from one or more sensors.

21. The implantable infusion device of claim 9, wherein the transceiver is configured to wirelessly transmit pumping catheter data selected from the group consisting of the following:

at least one programming parameter, a drug volume level, and sensor data.

22. The implantable infusion device of claim 9, wherein at least one pump includes two or more piezoelectric and/or electrostrictive pumps.

23. The implantable infusion device of claim 9, wherein the at least one pump includes a plurality of piezoelectric and/or electrostrictive pumps along a length of the at least one piezoelectric and/or electrostrictive mechanical pumping catheter.

* * * * *